United States Patent
Galambos et al.

(10) Patent No.: US 7,473,692 B2
(45) Date of Patent: Jan. 6, 2009

(54) SULFONAMIDE DERIVATIVES AS D3-RECEPTOR LIGANDS

(75) Inventors: János Galambos, Budapest (HU); Katalin Nógrádi, Budapest (HU); Éva Ágainé Csongor, Budapest (HU); György Miklós Keserü, Telki (HU); István Vágó, Budapest (HU); György Domány, Obánya (HU); Béla Kiss, Budapest (HU); István Gyertyán, Budapest (HU); István Laszlovszky, Budapest (HU); Judit Laszy, Nagykovácsi (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 462 days.

(21) Appl. No.: 10/491,150

(22) PCT Filed: Sep. 25, 2002

(86) PCT No.: PCT/HU02/00093

§ 371 (c)(1), (2), (4) Date: Oct. 22, 2004

(87) PCT Pub. No.: WO03/029233

PCT Pub. Date: Apr. 10, 2003

(65) Prior Publication Data

US 2005/0107397 A1  May 19, 2005

(30) Foreign Application Priority Data

Sep. 28, 2001 (HU) .................................. 103988

(51) Int. Cl.
- *A61K 31/4965* (2006.01)
- *A01N 43/40* (2006.01)
- *C07D 401/00* (2006.01)
- *C07D 295/00* (2006.01)
- *C07D 241/04* (2006.01)
- *C07D 211/00* (2006.01)
- *C07D 211/54* (2006.01)
- *C07D 211/40* (2006.01)
- *C07D 211/56* (2006.01)
- *C07D 211/92* (2006.01)
- *C07D 211/18* (2006.01)

(52) U.S. Cl. .............. 514/255.03; 514/327; 514/329; 544/363; 544/379; 544/360; 544/392; 546/216; 546/217; 546/223; 546/232

(58) Field of Classification Search .......... 514/255.03, 514/327, 329; 544/363, 379, 360, 392; 546/216–217, 546/223, 232

See application file for complete search history.

(56) References Cited

U.S. PATENT DOCUMENTS

| | | | |
|---|---|---|---|
| 5,047,406 A * | 9/1991 | Caprathe et al. | 514/253.01 |
| 5,872,119 A | 2/1999 | Wermuth et al. | 514/254 |
| 5,985,895 A | 11/1999 | Wermuth et al. | 514/317 |
| 6,084,130 A | 7/2000 | Romero et al. | |
| 6,274,593 B1 | 8/2001 | Johns et al. | |
| 6,414,154 B1 | 7/2002 | Vong | |
| 6,465,485 B1 | 10/2002 | Branch et al. | |
| 6,472,392 B1 | 10/2002 | Starck et al. | |
| 6,521,638 B1 | 2/2003 | Johnson et al. | |
| 6,583,166 B1 | 6/2003 | Starck et al. | |
| 6,605,607 B1 | 8/2003 | Hadley et al. | |
| 6,723,724 B2 | 4/2004 | Koh et al. | |

FOREIGN PATENT DOCUMENTS

| | | |
|---|---|---|
| EP | 0 779 284 A1 | 6/1997 |
| WO | WO 93/21179 | 10/1993 |
| WO | WO 97/45403 | 12/1997 |
| WO | WO 98/50364 | 11/1998 |

OTHER PUBLICATIONS

West, Anthony R., Solid State Chemistry and Its Applications, Wiley, New York, 1988, 358.*

Glase, S.A., et al., "4-Bromo-1-Methoxy-N-[2-(4-Aryl-1-Piperazinyl)Ethyl]-2-Naphthalenecarboxamides: Selective Dopamine D$_3$ Receptor Partial Agonists," *Bioorg. Med. Chem. Lett.* 6:1361-1366, Elsevier Science Ltd. (1996).

International Search Report for International Patent Application No. PCT/HU 02/00093, mailed on Nov. 20, 2002, European Patent Office, The Netherlands.

(Continued)

*Primary Examiner*—James O. Wilson
*Assistant Examiner*—Erich A Leeser
(74) *Attorney, Agent, or Firm*—Sterne, Kessler, Goldstein & Fox P.L.L.C.

(57) ABSTRACT

The present invention relates to new D$_3$ dopamine receptor subtype selectice ligands of formula (I) to pharmacological compositions containing the same and to their use in therapy and/or prevention of psychoses (e.g. schizophrenia, schizoaffective disorders, etc), drug (e.g. alcohol, cocaine and nicotine, opioids etc.) abuse, cognitive impairment accompanying schizophrenia, mild-to-moderate cognitive deficits, amnesia, eating disorders (e.g. bulimia nervosa, etc.), attention deficit disorders, hyperactivity disorders in children, psychotic depression, mania, paranoid and delusional disorders, dyskinetic disorders (e.g. Parkinson's diseases, neuroleptic induced Parkinson's dissases, tardive dyskinesias) anxiety, sexual dysfunction, sleep disorders, emesis, aggression, autism, pain ophthalmological diseases (e.g. glaucoma etc.).

(I)

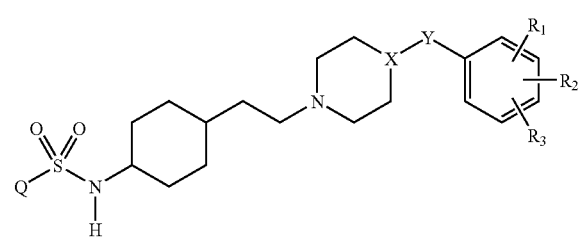

22 Claims, No Drawings

OTHER PUBLICATIONS

International Preliminary Examination Report for International Patent Application No. PCT/HU 02/00093, completed by Gellie, B.R., on May 21, 2003, European Patent Office, Germany.

Ágai-Csongor, É., et al., "Novel sulfonamides having dual dopamine D2 and D3 receptor affinity show in vivo antipsychotic efficacy with beneficial cognitive and EPS profile," *Bioorg. Med. Chem. Lett. 17*:5340-5344, Elsevier Science Ltd. (Oct. 2007).

Joyce, J.N., "Dopamine $D_3$ receptor as a therapeutic target for antipsychotic and antiparkinsonian drugs," *Pharmacol. Ther. 90*:231-259, Pergamon Press (May-Jun. 2001).

Levant, B., "The $D_3$ Dopamine Receptor: Neurobiology and Potential Clinical Relevance," *Pharmacol. Rev. 49*:231-252, American Society for Pharmacology and Experimental Therapeutics (1997).

* cited by examiner

SULFONAMIDE DERIVATIVES AS D3-RECEPTOR LIGANDS

FIELD OF THE INVENTION

The present invention relates to new $D_3$ dopamine receptor subtype selective ligands of formula (I) and/or geometric isomers and/or stereoisomers and/or diastereomers and/or salts and/or hydrates and/or solvates thereof which are useful in the therapy and/or prevention of psychoses (e.g. schizophrenia, schizo-affective disorders, etc.) and other central nervous system and ophthalmological disorders. The present invention also relates to the processes for producing compounds of formula (I) and to pharmacological compositions containing the same.

DESCRIPTION OF THE PRIOR ART

PCT Patent Publication WO 98/50364 describes tetrahydroisoquinoline derivatives which have affinity for dopamine receptors and useful as antipsychotic agents.

PCT Patent Publication WO 97/45403 discloses aryl substituted cyclic amines as selective dopamine $D_3$ ligands.

German Patent Publication DE 19728996 describes triazol derivatives. The compounds are said to be dopamine $D_3$ receptor antagonists and/or agonists useful for the treatment of central nervous system disorders e.g. Parkinson's disease or schizophrenia.

Although the compounds mentioned in the above publications have affinity for dopamine $D_3$ receptors, their chemical structures differ from the structure of compounds of the present invention.

SUMMARY OF THE INVENTION

We have found a class of sulfonamide derivatives which have high affinity for dopamine $D_3$ receptors and selectivity over other receptors, especially dopamine $D_2$. The selectivity is particularly important as the undesired side effects of the compounds are much less pronounced.

The present invention relates to new $D_3$ dopamine receptor subtype selective ligands having sulfonamide structures of formula (I)

(I)

wherein
X represents a nitrogen atom or CH group;
Y represents a bond when X stands for nitrogen, or an oxygen atom or NH or $CH_2$ or $OCH_2$ group when X stands for CH group;
$R_1$, $R_2$, $R_3$ may be the same or different and represent independently a substituent selected from hydrogen, halogen, $C_{1-6}$-alkyl, $C_{1-6}$ alkoxy, cyano, hydroxy, trifluoromethyl, $C_{1-6}$-alkylsulfonyloxy, trifluoromethanesulfonyloxy, $C_{1-6}$-alkanoyloxy, amino, alkylamino, alkanoylamino, alkylsulfonylamino, arylsulfonylamino, aminocarbonyl, carboxy, N-hydroxycarmamimidoyl, carbamimidoyl, hydroxycarbamoyl, thiocarbamoyl, sulfamoyl, mono or bicyclic heterocyclic group or optionally substituted phenyl, or two adjacent groups of $R_1$, $R_2$ and $R_3$ may combine to form an optionally substituted fused mono or bicyclic heterocyclic group;
Q represents a dialkylamino group or an optionally substituted alkyl, aryl, heteroaryl, aralkyl or heteroaralkyl group and/or geometric isomers and/or stereoisomers and/or diastereomers and/or salts and/or hydrates and/or solvates thereof, to the processes for producing the same, to the pharmacological compositions containing the same and their use in therapy and/or prevention of psychoses (e.g. schizophrenia, schizo-affective disorders, etc.), drug (e.g. alcohol, cocaine and nicotine, opioids etc.) abuse, cognitive impairment accompanying schizophrenia, mild-to-moderate cognitive deficits, amnesia, eating disorders (e.g. bulimia nervosa, etc.), attention deficit disorders, hyperactivity disorders in children, psychotic depression, mania, paranoid and delusional disorders, dyskinetic disorders (e.g. Parkinson's disease, neuroleptic induced Parkinsonism, tardive dyskinesias) anxiety, sexual dysfunction, sleep disorders, emesis, aggression, autism, pain, ophthalmological diseases (e.g. glaucoma etc.).

DETAILED DESCRIPTION OF THE INVENTION

The present invention relates to new compounds of formula (I)

(I)

wherein
X represents a nitrogen atom or CH group;
Y represents a bond when X stands for nitrogen, or an oxygen atom or NH or $CH_2$ or $OCH_2$ group when X stands for CH group;
$R_1$, $R_2$, $R_3$ may be the same or different and represent independently a substituent selected from hydrogen, halogen, $C_{1-6}$-alkyl, $C_{1-6}$ alkoxy, cyano, hydroxy, trifluoromethyl, $C_{1-6}$-alkylsulfonyloxy, trifluoromethanesulfonyloxy, $C_{1-6}$-alkanoyloxy, amino, alkylamino, alkanoylamino, alkylsulfonylamino, arylsulfonylamino, aminocarbonyl, carboxy, N-hydroxycarmamimidoyl, carbamimidoyl, hydroxycarbamoyl, thiocarbamoyl, sulfamoyl, mono or bicyclic heterocyclic group or optionally substituted phenyl, or two adjacent groups of $R_1$, $R_2$ and $R_3$ may combine to form an optionally substituted fused mono or bicyclic heterocyclic group;
Q represents a dialkylamino group or an optionally substituted $C_{1-6}$-alkyl, aryl, heteroaryl, aralkyl or heteroaralkyl group and/or geometric isomers and/or stereoisomers and/or diastereomers and/or salts and/or hydrates and/or solvates thereof.

When Q represents aryl, the aryl moiety may be selected from an optionally substituted mono- or bicyclic aryl namely phenyl or naphthyl group.

A heteroaryl ring in the meaning of Q may be monocyclic or bicyclic ring.

The monocyclic heteroaryl ring may be an optionally substituted 5- or 6-membered aromatic heterocyclic group containing 1 to 4 heteroatoms selected from O, N or S.

Examples of 5- and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl and pyrazolyl, preferably pyridyl and thienyl.

Examples of bicyclic heteroaromatic groups include indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl or isoquinolinyl, preferably quinolinyl, benzofuranyl, benzothiophenyl, benzthiazolyl, benzimidazolyl and indolyl group.

The substituents of substituted $C_{1-6}$-alkyl, aryl, heteroaryl, aralkyl or heteroaralkyl groups in the meaning of Q are selected from hydrogen, halogen, cyano, trifluoromethyl, $C_{1-6}$-alkyl, $C_{1-6}$-alkoxy, $C_{1-6}$-alkanoyl, methylenedioxy, $C_{1-6}$-alkylamino, $C_{1-6}$-alkanoylamino, optionally substituted aroyl, aryloxy, aminosulfonyl, arylsulfonylamido, optionally substituted mono or bicyclic aromatic or heteroaromatic ring, wherein the aryl may have the same meaning as mentioned above.

The substituents of $C_{1-6}$-alkanoyloxy in the meaning of $R_1$, $R_2$ and $R_3$ are selected from hydrogen or halogen.

The amino, aminoalkyl, aminocarbonyl, N-hydroxycarbamimidoyl, carbamimidoyl, hydroxycarbamoyl, thiocarbamoyl and sulfamoyl groups in the meaning of $R_1$, $R_2$ and $R_3$ may optionally be substituted on the N atom.

The mono or bicyclic heterocyclic group in the meaning of $R_1$, $R_2$ and $R_3$ may be saturated or unsaturated containing 1 to 4 heteroatoms selected from O, N or S.

In the compounds of formula (I) an alkyl group or moiety in alkoxy, alkanoyl, alkanoylamino, alkanoyloxy groups may be straight or branched included methyl, ethyl, n-propyl, n-butyl, n-pentyl-, n-hexyl and branched isomers thereof such as isopropyl, t-butyl, sec-butyl, and the like.

The halogen substituent(s) in the compounds of formula (I) may be fluorine, chlorine, bromine or iodine, preferably fluorine, bromine and chlorine.

The compounds of formula (I) can exist in the form of cis- and trans-isomers with respect to the configuration of the cyclohexane ring. These and their mixtures are likewise within the scope of the present invention. Preferably the compounds of the invention are in the trans configuration.

The invention also relates to the salts of compounds of formula (I) formed with acids.

Both organic and inorganic acids can be used for the formation of acid addition salts. Suitable inorganic acids can be for example hydrochloric acid, sulfuric acid, nitric acid and phosphoric acid. Representatives of monovalent organic acids can be for example formic acid, acetic acid, propionic acid, and different butyric acids, valeric acids and capric acids. Representatives of bivalent organic acids can be for example oxalic acid, malonic acid, maleic acid, fumaric acid and succinic acid. Other organic acids can also be used, such as hydroxy acids for example citric acid, tartaric acid, or aromatic carboxylic acids for example benzoic acid or salicylic acid, as well as aliphatic and aromatic sulfonic acids for example methanesulfonic acid, naphtalenesulfonic acid and p-toluenesulfonic acid. Especially valuable group of the acid addition salts is in which the acid component itself is physiologically acceptable and does not have therapeutical effect in the applied dose or it does not have unfavourable influence on the effect of the active ingredient. These acid addition salts are pharmaceutically acceptable acid addition salts. The reason why acid addition salts, which do not belong to the pharmaceutically acceptable acid addition salts belong to the present invention is, that in given case they can be advantageous in the purification and/or isolation of the desired compounds.

Solvates and hydrates of compounds of formula (I) are also included within the scope of the invention.

As the invention relates also to the salts of compounds of formula (I) formed with acids, especially the salts formed with pharmaceutically acceptable acids, the meaning of compound of formula (I) is either the free base or the salt even if it is not referred separately.

Preferred compounds of the invention are those compounds of formula (I)

(I)

wherein

X represents a nitrogen atom or CH group;

Y represents a bond when X stands for nitrogen, or an oxygen atom or NH or $CH_2$ or $OCH_2$ group when X stands for CH group;

$R_1$, $R_2$, $R_3$ may be the same or different and represent independently hydrogen, alkyl, alkoxy, halogen, cyano, aminocarbonyl, trifluoromethyl, amino, alkylamino, alkanoylamino, alkylsulfonylamino, arylsulfonylamino, aminocarbonyl, carboxy, N-hydroxycarmamimidoyl, carbamimidoyl, hydroxycarbamoyl, thiocarbamoyl, sulfamoyl, mono or bicyclic heterocyclic group or optionally substituted phenyl, or two adjacent groups of $R_1$, $R_2$ and $R_3$ may combine to form an optionally substituted fused mono or bicyclic heterocyclic group;

Q represents dialkylamino, optionally substituted phenyl, biphenyl, pyridyl, thienyl, alkyl or quinolinyl;

and/or geometric isomers and/or stereoisomers and/or diastereomers and/or salts and/or hydrates and/or solvates thereof.

Especially preferred compounds of the invention are those compounds of formula (I)

(I)

wherein

X represents a nitrogen atom or CH group;

Y represents a bond when X stands for nitrogen, or $CH_2$ group when X stands for CH group;

$R_1$, $R_2$, $R_3$ may be the same or different and represent independently hydrogen, fluorine, bromine, chlorine atoms or cyano, trifluoromethyl, methyl, methoxy, ethoxy, aminocarbonyl, amino, alkylamino, alkanoylamino, alkylsulfonylamino, arylsulfonylamino, aminocarbonyl, carboxy, N-hydroxycarmamimidoyl, carbamimidoyl, hydroxycarbamoyl, thiocarbamoyl, sulfamoyl, mono or bicyclic heterocyclic group or optionally substituted phenyl, or two adjacent groups of $R_1$, $R_2$ and $R_3$ may combine to form an optionally substituted fused mono or bicyclic heterocyclic group;

Q represents $C_{1-4}$ alkyl, dimethylamino, biphenyl, alkylphenyl, alkoxyphenyl, halophenyl, nitrophenyl, trifluoromethylphenyl or aminocarbonylmethylphenyl, pyridyl, or quinolinyl;

and/or geometric isomers and/or stereoisomers and/or diastereomers and/or salts and/or hydrates and/or solvates thereof.

Furthermore subjects of the present invention are the synthesis of compounds of formula (I) and the chemical and pharmaceutical manufacture of medicaments containing these compounds, as well as the process of treatments and/or prevention with these compounds, which means administering to a mammal to be treated—including human—effective amount/amounts of compounds of formula (I) of the present invention as such or as medicament.

The present invention also provides processes for preparing compounds of formula (I) by forming a sulfonamide bond between a sulfochloride of formula (II) or a derivative thereof (II)

wherein the meaning of Q is as described above for the formula (I) and an amine of formula (III) or a derivative thereof (III)

wherein the meaning of $R_1$, $R_2$, $R_3$, X and Y are as described above for the formula (I).

The sulfonamide bond formation may be carried out by known methods, preferably by reacting a sulfochloride of formula (II) with an amine of formula (III) in the presence of a base. The amine of formula (III) as a base or as a salt formed with an acid is dissolved in an appropriate solvent (for example chlorinated hydrocarbons, hydrocarbons, tetrahydrofuran, dimethylformamide or acetonitrile), base is added (for example triethylamine) followed by the appropriate sulfochloride. The reaction is carried out preferably between −10° C. and ambient temperature. The reactions are followed by thin layer chromatography. The necessary reaction time is about 6-24 h. The work-up of the reaction mixture can be carried out by different methods. The products can be purified for example by crystallization or, if necessary, by column chromatography.

Those having skill in the art can recognize that the starting materials may be varied and additional steps can be employed to produce compounds encompassed by the present invention, as demonstrated by the Examples. In some cases protection of certain reactive functionalities may be necessary to achieve some of the above transformations. In general the need for such protecting groups is apparent to those skilled in the art as well as the conditions necessary to attach and remove such groups.

The structures of all intermediates and end products were elucidated by IR, NMR and mass spectroscopy.

The sulfochlorides of formula (II) are either commercially available or can be synthesized by different known methods, e.g. J.Chem.Soc., 1992, 4889-4898; J.Med.Chem.,1989, 32, 2436-2442; J.Med.Chem., 1993, 36, 320-330.

The amines of formula (III) may be prepared by alkylation of compounds of formula (IV) or a derivative thereof (IV)

wherein the meaning of $R_1$, $R_2$, $R_3$, X and Y are as described above for formula (I), by known methods: e.g. J.Med.Chem., 2000, 43, 1878-1885.

The amines of formula (IV) are either commercially available or can be synthesized by different known methods: e.g. where X stands for CH and Y stands for NH group: Synlett, 1961, 537; where X stands for CH and Y stands for oxygen or $OCH_2$: J.Med.Chem., 1974, 17, 1000; where X stands for CH and Y stands for $CH_2$ group: U.S. Pat. No. 3,632,767; WO 97/23216; FR 2,534,580; where Y is a bond and X stands for nitrogen: Tetrahedron, 1999, 55, 13285-13300; J.Med. Chem., 1989, 32, 1052-1056; U.S. Pat. No. 2,922,788.

The separation of cis- and trans-isomers either of compounds of formula (I) or of formula (III) or the protected derivatives of the latter is carried out by conventional methods, e.g. by chromatography and/or crystallization, or the cis- or trans-isomers of formula (III) can be prepared using pure cis- or trans-isomers as an alkylating agents.

The obtained derivatives of formula (I) can be transformed into an other compound of formula (I) in given case by introducing further substituent(s) and/or modifying and/or removing the existing one(s). For example cleaving the methyl group from a methoxy group which stands for $R_1$ and/or $R_2$ and/or $R_3$ leads to phenol derivatives. The cleavage of methyl group can be carried out for example with boron tribromide in dichloromethane. The compounds of formula (I) containing cyano groups can be for example transformed to amides by hydrolysing them with hydrogenperoxide in dimethylsulfoxide, or to amidines by reacting them first with gaseous hydrogenchloride in ether, then by reacting the iminoester obtained with ammonia, etc.

The sulfonamide derivatives of formula (I) can also be prepared on solid support:

i) A compound of formula (VI) wherein $R_6$ represents hydrogen or a protecting group e.g. silyl or tetrahydropyranyl was attached to a polystyrene resin of formula (V), wherein $R_4$ and $R_5$ can be the same or different and represent hydrogen or methoxy group with the exception $R_4$=$R_5$=H, by reductive amination with a reducing agent e.g. $NaB(OAc)_3H$ or $NaBH_3CN$;

ii) halogenation, preferably bromination, of the terminal hydroxy group of a compound of formula (VII), wherein the meaning of $R_6$ is as described above for formula (VI), with a halogenation agent e.g. $PPh_3Br_2$, $PPh_3I_2$, or if it was protected, the protecting group had been removed before the halogenation, which results a solid phase compound of formula (VIII) wherein Z represents halogen, preferably bromide and the meaning of $R_4$ and $R_5$ is as described above for formula (V);

iii) sulfonylation a compound of formula (VIII) with different sulfochlorides of formula (II) wherein the meaning of Q is as described above for formula (I) (the first combinatorial step);

iv) alkylation with a compound of formula (IX) wherein the meaning of Z, $R_4$ and $R_5$ are as described above for the formula (VIII) and the meaning of Q is as described above for formula (I) of a secondary amine of formula (IV) wherein the meaning of $R_1$, $R_2$, $R_3$, X and Y are as described above for the formula (I) (the second combinatorial step);

v) releasing the products of formula (I) from the solid-phase compounds of formula (X) wherein the meaning of Q, $R_1$, $R_2$, $R_3$, X and Y are as described above for the formula (I) and of $R_4$ and $R_5$ are as described above for the formula (V) by acidic cleavage.

Figure 1:
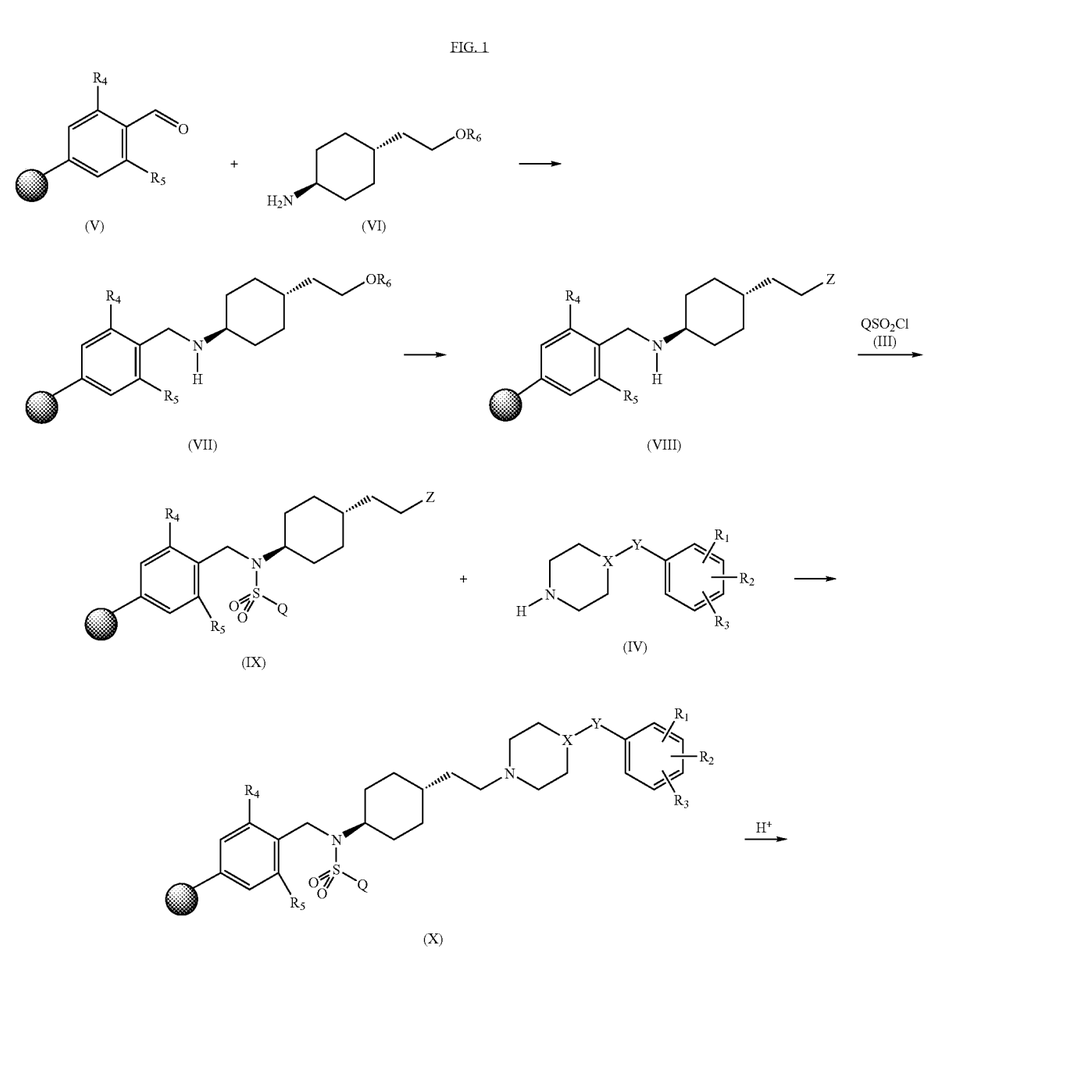

This synthetic route is represented by FIG. 1.

FIG. 1

(I)

The invention also relates to the pharmaceutical compositions containing the compounds of formula (I) as active ingredient.

The compounds of formula (I) of the present invention have been found to exhibit affinity for dopamine receptors, in particular the $D_3$ receptor, and are expected to be useful in the treatment of disease states which require modulation of such receptors, e.g. psychotic or ophthalmological disorders. The compounds of formula (I) have been found to have greater affinity for dopamine $D_3$ than for $D_2$ receptors. The compounds of formula (I) may therefore advantageously be used as selective modulators of $D_3$ receptors.

Dysfunction of the dopaminergic neurotransmitter system is involved in the pathology of several neuropsychiatric disorders such as schizophrenia, Parkinson's disease and drug abuse. The effect of dopamine is mediated via at least five distinct dopamine receptors belonging to the $D_1$-($D_1$, $D_5$) or the $D_2$-($D_2$, $D_3$, $D_4$) families. $D_3$ receptors have been shown to have characteristic distribution in the cerebral dopaminergic systems. Namely, high densities were found in certain limbic structures such as nucleus accumbens and islands of Calleja. Therefore, selective targeting of the $D_3$ receptors may be a promising approach for more selective modulation of dopaminergic functions and consequently for successful therapeutic intervention in several abnormalities, such as schizophrenia, emotional or cognitive dysfunctions and addiction (Sokoloff, P. et al: Nature, 1990, 347, 146; Schwartz, J.-C. et al.: Clin. Neuropharmacol., 1993, 16, 295; Levant, B.: Pharmacol. Rev., 1997, 49, 231.), addiction (Pilla, C. et al: Nature, 1999, 400, 371) and Parkinson's disease (Levant, B. et al.: CNS Drugs, 1999, 12, 391) or pain (Levant, B. et al.: Neurosci. Lett., 2001, 303, 9). Dopamine $D_3$ receptors are also implicated in regulation of intraocular pressure and agonists at these receptors are capable of decreasing the intraocular pressure (Chu, E. et al: J. Pharmacol. Exp. Ther., 2000, 292, 710), thus $D_3$ receptors agonists can be useful for the treatment of glaucoma.

Certain compounds of formula (I) have been found to be dopamine $D_3$ receptor antagonist, others may be agonists or partial agonists.

In a further aspect of the present invention provides a method of treating conditions which require modulation of dopamine $D_3$ receptors, for example psychoses, for example in the treatment of schizophrenia, schizo-affective disorders, psychotic depression, mania, paranoid and delusional disorders, dyskinetic disorders such as Parkinson's disease, neuroleptic induced parkinsonism, depression, anxiety, memory disorders, sexual dysfunction, drug dependency and ophthalmological disorders which comprises administering to a subject in need thereof an effective amount of a compound of formula (I) or a physiologically acceptable salt thereof.

The invention also provides the use of a compound of formula (I) and/or geometric isomers and/or stereoisomers and/or diastereomers and/or physiologically acceptable salts and/or hydrates and/or solvates thereof in the manufacture of a medicament for the treatment of conditions which require modulation of dopamine $D_3$ receptors.

A preferred use for $D_3$ agonists or partial agonists according to the present invention is in the treatment of drug abuse (such as cocaine abuse etc.) and eye diseases (such as glaucoma).

A preferred use for $D_3$ antagonists according to the present invention is in the treatment of schizophrenia, schizo-affective disorders, psychotic depression, mania, paranoid and delusional disorders, dyskinetic disorders such as Parkinson's disease, neuroleptic induced parkinsonism, depression, anxiety, memory disorders, sexual dysfunction, drug abuse, pain.

For use in medicine, the compounds of formula (I) and/or geometric isomers and/or stereoisomers and/or diastereomers and/or physiologically acceptable salts and/or hydrates and/or solvates thereof are usually administered as a standard pharmaceutical composition. The present invention therefore provides in a further aspect pharmaceutical compositions comprising a new compound of formula (I) and/or geometric isomers and/or stereoisomers and/or diastereomers and/or physiologically acceptable salts and/or hydrates and/or solvates thereof and one or more physiologically acceptable carrier(s).

The compounds of formula (I) and/or geometric isomers and/or stereoisomers and/or diastereomers and/or physiologically acceptable salts and/or hydrates and/or solvates thereof may be administered by any convenient method, for example by oral, parental, buccal, sublingual, nasal, rectal or transdermal administration and the pharmaceutical compositions adapted accordingly.

The compounds of formula (I) and/or geometric isomers and/or stereoisomers and/or diastereomers and/or physiologically acceptable salts and/or hydrates and/or solvates thereof and the physiologically acceptable salts thereof which are active when given orally can be formulated as liquids or solids, for example syrups, suspensions or emulsions, tablets, capsules and lozenges.

A liquid formulation of the compounds of formula (I) and/or geometric isomers and/or stereoisomers and/or diastereomers and/or physiologically acceptable salts and/or hydrates and/or solvates thereof generally consists of a suspension or solution of the compound of formula (I) or physiologically acceptable salts thereof in a suitable liquid carrier(s) for example an aqueous solvent, such as water, ethanol or glycerine, or a non-aqueous solvent, such as polyethylene glycol or an oil. The formulation may also contain a suspending agent, preservative, flavouring or colouring agent.

A composition in the solid form of a tablet can be prepared using any suitable pharmaceutical carrier(s) routinely used for preparing solid formulations. Examples of such carriers include magnesium stearate, starch, lactose, sucrose, cellulose etc.

A composition in the solid form of a capsule can be prepared using routine encapsulation procedures. For example, pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Typical parenteral compositions consist of a solution or suspension of the compound of formula (I) and/or geometric isomers and/or stereoisomers and/or diastereomers and/or physiologically acceptable salts and/or hydrates and/or solvates thereof or physiologically acceptable salt thereof in a steril aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions of the present invention for nasal administration containing a compound of formula (I) and/or geometric isomers and/or stereoisomers and/or diastereomers and/or physiologically acceptable salts and/or hydrates and/or solvates thereof may conveniently be formulated as aerosols, drops, gels and powders. Aerosol formulations of the present invention typically comprise a solution or fine suspension of the compound of formula (I) in a physiologically acceptable aqueous or non-aqueous solvent and are usually presented in a single or multidose quantities in steril form is a sealed container, which can take the form of a cartridge or refill for use with an atomising device. Alternatively, the sealed container may be a unitary dispensing device, such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas, such as compressed air or an organic propellant, such as a fluorochlorohydrocarbon. The aerosol dosages form can also take the form of a pump-atomiser. Compositions of the present invention containing a compound of formula (I) suitable for buccal or sublingual administration include tablets, lozenges and pastilles, wherein the active ingredient is formulated with a carrier, such as sugar and acacia, tragacanth, or gelatine and glycerin etc.

Compositions of the present invention containing a compound of formula (I) and/or geometric isomers and/or stereoisomers and/or diastereomers and/or physiologically acceptable salts and/or hydrates and/or solvates thereof for rectal administration are conveniently in the form of suppositories containing a conventional suppisiory base, such as cocoa butter.

Compositions of the present invention containing a compound of formula (I) and/or geometric isomers and/or stereoisomers and/or diastereomers and/or physiologically acceptable salts and/or hydrates and/or solvates thereof for transdermal administration include ointments, gels and patches.

The compositions of the present invention containing a compound of formula (I) and/or geometric isomers and/or stereoisomers and/or diastereomers and/or physiologically acceptable salts and/or hydrates and/or solvates thereof is preferably in the unit dose form, such as tablet, capsule or ampoule.

Each dosage unit of the present invention for oral administration contains preferably from 1 to 250 mg of a compound of formula (I) and/or geometric isomers and/or stereoisomers and/or diastereomers and/or physiologically acceptable salts and/or hydrates and/or solvates thereof calculated as a free base.

Each dosage unit of the present invention for parenteral administration contains preferably from 0.1 to 25 mg of a compound of formula (I) and/or geometric isomers and/or stereoisomers and/or diastereomers and/or physiologically acceptable salts and/or hydrates and/or solvates thereof calculated as a free base.

The physiologically acceptable compounds formula (I) and/or geometric isomers and/or stereoisomers and/or diastereomers and/or physiologically acceptable salts and/or hydrates and/or solvates thereof can normally be administered in a daily dosage regimen (for an adult patient) of, for example, an oral dose between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of formula (I) and/or geometric isomers and/or stereoisomers and/or diastereomers and/or physiologically acceptable salts and/or hydrates and/or solvates thereof calculated as the free base. The compound of the present invention can be administered 1 to 4 times per day. The compound of the present invention can suitably be administered for a period of continous therapy, for example for a week or more.

Receptor Binding Assays

1. $D_3$ receptor binding

Binding study was carried out on rat recombinant $D_3$ receptors expressed in Sf9 cells using [$^3$H]-spiperone (0.4 nM) as ligand and haloperidol (10 μM) for determination of non-specific binding. The assay was performed according to Research Biochemical International assay protocol for $rD_3$ receptor (Cat. No. D-181).

2. $D_2$ Receptor Binding

Binding of [$^3$H]-spiperone (0.5 nM) to rat striatal tissue was measured according to the method of Seeman (J. Neurochem., 1984, 43 221-235). The non-specific binding was determined in the presence of (±)-sulpiride (10 μM).

$D_3$ and $D_2$ receptor binding data of compounds of the present invention are listed in Table 1.

TABLE 1

| code | $D3-IC_{50}$ (nM) | $D2-IC_{50}$ (nM) |
|---|---|---|
| 70001485 | 5.5 | 2586 |
| 70001488 | 4.3 | 245 |
| 70001492 | 2.0 | 65 |
| 70001588 | 2.5 | 102 |
| 70001589 | 3.0 | 16 |
| 70001596 | 0.6 | 110 |
| 70001766 | 5.3 | 128 |
| 70001788 | 1.5 | 290 |
| 70001934 | 1.0 | 109 |
| 70001935 | 0.3 | 29 |
| 70001686 | 3.9 | 345 |
| 70001875 | 2.8 | 66 |

The most prominent side effects of the first generation antipsychotic compounds (e.g. chlorpromazine and haloperidol) with preferential blockade at dopamine $D_2$, and alpha-1 receptors, are the tardive dyskinesia and orthostatic hypotension. The former one is the result of blockade of $D_2$ receptors in the basal ganglia whereas the latter is the consequence of antagonism of alpha-1 receptors.

Compounds in Table 1 are potent ligands at $D_3$ receptors (IC-50 values are between 0.3 and 5.5 nM) and show 5 to 470 fold selectivity over $D_2$ receptors. Moreover, the compounds have beneficial profile in terms of potency on $D_3$ receptors and selectivity towards $D_2$. It is therefore anticipated that no or greatly diminished adverse effects related to $D_2$ receptors will occur in the course of therapeutical application of compounds of the present invention.

The invention is further illustrated by the following non-limiting examples.

EXAMPLE 1

1-(3-cyano-5-trifluoromethyl-phenyl)-piperazine 2.42 g (13 mmol) 3-fluoro-5-trifluoromethyl-benzonitrile and 6.0 g (70 mmol) piperazine was dissolved in 50 ml dimethylsulfoxide and the solution was refluxed for one day. The mixture was poured into 200 ml of water and extracted with diethylether (3×100 ml). The organic layers were washed with saturated sodium chloride solution, then dried and evaporated to dryness in vacuo giving 2.96 g (yield 89.2%) of the title compound, melting at 85-7° C.

EXAMPLE 1

Trans-(4-{2-[4-(3-cyano-5-trifluoromethyl-phenyl)-piperazin-1-yl]-ethyl}-cyclohexyl)-carbamic acid tert-butyl ester 0.63 g (2.5 mmol) of 1-(3-cyano-5-trifluoromethyl-phenyl)-piperazine and 0.6 g (2.5 mmol) of trans-2-{1-[4-(N-tert-butyloxycarbonyl)amino]cyclohexyl}-acetaldehyde were dissolved in dichloroethane (35 ml), 0.79 g (3.7 mmol) sodium triacetoxyborohydride was added portionswise and the reaction mixture was stirred for 20 hours at ambient temperature, then 20% potassium carbonate solution in water (20 ml) was added. The organic layer was separated, dried and evaporated to dryness in vacuo. The precipitate was recrystallized from acetonitrile to give the title compound 1.03 g (yield 85.8%), m.p.: 139-140° C.

The Following Compounds were Prepared in a Similar Manner to Example 1:

Trans-(4-{2-[4-(3-methoxy-biphenyl)-4-yl)-piperazin-1-yl]-ethyl}-cyclohexyl)-carbamic acid tert-butyl ester, m.p.: 171-2° C.

Trans-(4-{2-[4-(3-trifluoromethyl-phenyl)-piperazin-1-yl]-ethyl}-cyclohexyl)-carbamic acid tert-butyl ester, m.p.: 130-2° C.

Trans-(4-{2-[4-(2,3-dichloro-phenyl)-piperazin-1-yl]-ethyl}-cyclohexyl)-carbamic acid tert-butyl ester, m.p.: 144-5° C.

Trans-(4-{2-[4-(3-trifluoromethyl-phenylmethyl)-piperidin-1-yl]-ethyl}-cyclohexyl)-carbamic acid tert-butyl ester, m.p.: 107° C.

Trans-(4-{2-[4-(3-fluoro-phenylmethyl)-piperidin-1-yl]-ethyl}-cyclohexyl)-carbamic acid tert-butyl ester, m.p.: 128° C.

Trans-(4-{2-[4-(3-cyano-phenylmethyl)-piperidin-1-yl]-ethyl}-cyclohexyl)-carbamic acid tert-butyl ester, m.p.: 115-6° C.

Trans-(4-{2-[4-(3-trifluoromethyl-phenylamino)-piperidin-1-yl]-ethyl}-cyclohexyl)-carbamic acid tert-butyl ester, m.p.: 112-3° C.

Trans-(4-{2-[4-(3-trifluoromethyl-phenylmethoxy)-piperidin-1-yl]-ethyl}-cyclohexyl)-carbamic acid tert-butyl ester, m.p.: 107° C.

Trans-(4-{2-[4-(3-trifluoromethyl-phenoxy)-piperidin-1-yl]-ethyl}-cyclohexyl)-carbamic acid tert-butyl ester, m.p.: 118-9° C.

EXAMPLE 2

Trans-3-{4-[2-(4-amino-cyclohexyl)-ethyl]-piperazin-1-yl}-5-trifluoromethyl-benzonitrile 1.03 g (2.1 mmol) trans-(4-{2-[4-(3-cyano-5-trifluoromethyl-phenyl)-piperazin-1-yl]-ethyl}-cyclohexyl)-carbamic acid tert-butyl ester was deprotected at 10° C. using 10 ml ethylacetate saturated with gaseous hydrochloric acid, the precipitate was filtered giving 0.94 g (yield 98%) dihydrochloride salt of the title compound, melting above 260° C.

The Following Compounds were Prepared in a Similar Manner to Example 2:

Trans-4-{2-[4-(3-methoxy-biphenyl-4-yl)-piperazin-1-yl]-ethyl}-cyclohexylamine dihydrochloride, m.p.: >280° C.

Trans-4-{2-[4-(3-trifluoromethyl-phenyl)-piperazin-1-yl]-ethyl}-cyclohexylamine dihydrochloride, m.p.: 280° C.

Trans-4-{(2-[4-(2,3-dichloro-phenyl)-piperazin-1-yl]-ethyl}-cyclohexylamine dihydrochloride, m.p.: 264-5° C.

Trans-4-{2-[4-(3-trifluoromethyl-phenylmethyl)-piperidin-1-yl]-ethyl}-cyclohexylamine dihydrochloride, m.p.: 268° C.

Trans-4-{2-[4-(3-fluoro-phenylmethyl)-piperidin-1-yl]-ethyl}-cyclohexylamine dihydrochloride, m.p.: 286-7° C.

Trans-4-{2-[4-(3-cyano-phenylmethyl)-piperidin-1-yl]-ethyl}-cyclohexylamine dihydrochloride, m.p.: 257-8° C.

Trans-4-{2-[4-(3-trifluoromethyl-phenylamino)-piperidin-1-yl]-ethyl}-cyclohexylamine dihydrochloride, m.p.: 260-4° C.

Trans-4-{2-[4-(3-trifluoromethyl-phenylmethoxy)-piperidin-1-yl]-ethyl}-cyclohexylamine dihydrochloride, m.p.: 262° C.

Trans-4-{2-[4-(3-trifluoromethyl-phenoxy)-piperidin-1-yl]-ethyl}-cyclohexylamine dihydrochloride, m.p.: 294° C.

EXAMPLE 3

Trans-N-(4-{2-[4-(3-cyano-5-trifluoromethyl-phenyl)-piperazin-1-yl]-ethyl}-cyclohexyl)-pyridin-3-sulfonamide (70001503)

0.38 g (1 mmol) of trans-3-{4-[2-(4-amino-cyclohexyl)-ethyl]-piperazin-1-yl}-5-trifluoromethyl-benzonitrile was dissolved in dichloromethane (30 ml), 0.42 ml (3 mmol) triethylamine was then added followed by 0.24 g (1.1 mmol) of pyridine-3-sulfochloride hydrochloride. The mixture was stirred for 24 hours, washed twice with 10% sodium bicarbonate solution, dried and evaporated to dryness in vacuo. The residue was purified on silica gel eluting with 10% ethanol/chloroform, then converted to the dihydrochloride salt of the title compound. 0.32 g (yield 54%), melting at 194-5° C.

The Following Compounds were Prepared in a Similar Manner to Example 3:

Trans-N'-(4-{2-[4-(3-methoxy-biphenyl-4-yl)-piperazin-1-yl]-ethyl}-cyclohexyl)-N,N-dimethyl hydrochloride, m.p.: 243-6° C. (70001488)

Trans-4-chloro-N-(4-{2-[4-(3-cyano-5-trifluoromethyl-phenyl)-piperazin-1-yl]-ethyl}-cyclohexyl)-benzenesulfonamide hydrochloride, m.p.: 260-2° C. (70001492)
Trans-4-chloro-N-(4-{2-[4-(3-trifluoromethyl-phenyl)-piperazin-1-yl]-ethyl}-cyclohexyl)-benzenesulfonamide hydrocloride, m.p.:223° C. (70001552)
Trans-N-(4-{2-[4-(3-methoxy-biphenyl-4-yl)-piperazin-1-yl]-ethyl}-cyclohexyl)-3-pyridinesulfonamide dihydrochloride, m.p.: 219° C. (70001737)
Trans-5-chloro-N-(4-{2-[4-(3-cyano-5-trifluoromethyl-phenyl)-piperazin-1-yl]-ethyl}-cyclohexyl)-2-thiophenesulfonamide hydrochloride, m.p.: 181° C. (70001766)
Trans-N'-(4-{2-[4-(3-cyano-5-trifluoromethyl-phenyl)-piperazin-1-yl]-ethyl}-cyclohexyl)-N,N-dimethyl-sulfamide, m.p.: 83-5° C. (70001788)
Trans-N-(4-{2-[4-(3-methoxy-biphenyl-4-yl)-piperazin-1-yl]-ethyl}-cyclohexyl)-buthanesulfonamide hydrochloride, m.p.: 215-8° C. (70001485)
Trans-N-(4-{2-[4-(3-trifluoromethyl-phenyl)-piperazin-1-yl]-ethyl}-cyclohexyl)-buthanesulfonamide hydrochloride, m.p.: 228-9° C. (70001596)
Trans-N-(4-{2-[4-(3-trifluoromethyl-phenyl)-piperazin-1-yl]-ethyl}-cyclohexyl)-4-morpholinepropanesulfonamide dihydrochloride, m.p.: 218-20° C. (70001934)
Trans-N-(4-{2-[4-(3-trifluoromethyl-phenyl)-piperazin-1-yl]-ethyl}-cyclohexyl)-3-pyridinesulfoamide dihydrochloride, m.p.: 183-6° C. (70001935)
Trans-N-(4-{2-[4-(2,3-dichloromethyl-phenyl)-piperazin-1-yl]-ethyl}-cyclohexyl)-3-pyridinesulfonamide dihydrochloride, m.p.: 272-4° C. (70002127)
Trans-4-bromo-N-(4-{2-[4-(3-trifluoromethyl-phenylmethyl)-piperidin-1-yl]-ethyl}-cyclohexyl)-benzenesulfonamide m.p.: 145° C. (70001539)
Trans-4-chloro-N-(4-{2-[4-(3-fluoro-phenylmethyl)-piperidin-1-yl]-ethyl}-cyclohexyl)-benzenesulfonamide m.p.: 109° C. (70001686)
Trans-N-(4-{2-[4-(3-trifluoromethyl-phenylmethyl)-piperidin-1-yl]-ethyl}-cyclohexyl)-3-pyridinesulfonamide dihydrochloride, m.p.: 102° C. (70002060)
Trans-4-chloro-N-(4-{2-[4-(3-trifluoromethyl-phenylmethyl)-piperidin-1-yl]-ethyl}-cyclohexyl)-benzenesulfonamide m.p.: 150-1° C. (70001317)
Trans-4-chloro-N-(4-{2-[4-(3-cyano-phenylmethyl)-piperidin-1-yl]-ethyl}-cyclohexyl)-benzenesulfonamide hydrochloride, m.p.: 101° C. (70001775)
Trans-N-(4-{2-[4-(3-trifluoromethyl-phenylamino)-piperidin-1-yl]-ethyl}-cyclohexyl)-trifluoroethanesulfonamide hydrochloride, m.p.: 198° C. (70001595)
Trans-N-(4-{2-[4-(3-trifluoromethyl-phenylamino)-piperidin-1-yl]-ethyl}-cyclohexyl)-buthanesulfonamide hydrochloride, m.p.: 198° C. (70001588)
Trans-4-chloro-N-(4-{2-[4-(3-trifluoromethyl-phenylamino)-piperidin-1-yl]-ethyl}-cyclohexyl)-benzenesulfonamide hydrochloride, m.p.: 237-9° C. (70001589)
Trans-N'-(4-{2-[4-(3-trifluoromethyl-phenylamino)-piperidin-1-yl]-ethyl}-cyclohexyl)-N,N-dimethylsulfamide hydrochloride, m.p.: 169-71° C. (70001590)
Trans-N-(4-{2-[4-(3-trifluoromethyl-phenylmethoxy)-piperidin-1-yl]-ethyl}-cyclohexyl)-3-pyridinesulfonamide dihydrochloride, m.p.: 73° C. (70001873)
Trans-N-(4-{2-[4-(3-trifluoromethyl-phenoxy)-piperidin-1-yl]-ethyl}-cyclohexyl)-3-pyridinesulfonamide dihydrochloride, m.p.: 98° C. (70001875)

EXAMPLE 4

Trans-N-{4-[2-[4-(3-aminocarbonyl-5-trifluoromethyl-phenyl)-1-piperizinyl]-ethyl]-cyclohexyl}-3-pyridinesulfonamide (70002080)

0.37 g (0.7 mmol) of trans-N-(4-{2-[4-(3-cyano-5-trifluoromethyl-phenyl)-piperazin-1-yl]-ethyl}-cyclohexyl)-pyridine-3-sulfonamide was dissolved in 2 ml dimethylsulfoxide, 80 mg $K_2CO_3$ was added and 0.15 ml of 30% $H_2O_2$ was dropped in while keeping the temperature at 20° C. After stirring for 2 h 20 ml of water was added, the precipitate filtered, washed with water giving the title compound, melting point:191° C. (0.2 g; 53%).

EXAMPLE 5

Polymer-bound trans-2-(4-amino-cyclohexyl)-ethanol 5 g of 2-(4-formyl-3-methoxy)phenoxyethyl polystyrene (1.12 mmol/g) resin was suspended in 150 ml of dichloromethane. To the shaken suspension 3.5 g (4.5 eq.) of trans-2-(4-amino-cyclohexyl)-ethanol was added, followed by dropwise addition of 4.5 ml of acetic acid. 1.2 g (1 eq) of NaBH(OAc)$_3$ was added in portions within 15 minutes. After 3 hours of shaking another 0.6 g (0.5 eq.) of NaBH(OAc)$_3$ was added in one portion. The shaking was continued overnight. The mixture was filtered and the resin was washed in sequence with the following solvents (100 ml, twice with each): dichloromethane, methanol, 10% triethylamine in dimethylformamide, methanol, dimethylformamide, tetrahydrofuran, diethylether.

EXAMPLE 6

Polymer-bound trans-2-(4-amino-cyclohexyl)-ethylbromide

The freshly prepared mixture of 1.45 g (5 eq.) triphenylphosphine and 0.28 ml (5 eq.) Br$_2$ in 20 ml of dichloromethane was added to 1 g of the polymer-bound trans-2-(4-amino-cyclohexyl)-ethanol and 0.38 g (5 eq.) 1-H-imidazole. The suspension was shaken for 18 hours, filtered and the resin was washed in sequence with the following solvents (20 ml, twice with each): dichloromethane, methanol, 10% triethylamine in dimethylformamide, methanol, dimethylformamide, tetrahydrofuran, diethylether.

EXAMPLE 7

Polymer-bound trans-4-bromo-N-[4-(2-bromo-ethyl)-cyclohexyl]-benzenesulfonamide

To 0.1 g of polymer-bound trans-2-(4-amino-cyclohexyl)-ethylbromide in 2.5 ml of tetrahydrofuran 10 mg dimethylaminopyridine, 0.07 ml (5 eq.) triethylamine and 0.13 g (5 eq.) 4-bromobenzenesulfochloride were added. The mixture was shaken for 18 hours, filtered and the resin was washed in sequence with the following solvents (10 ml, twice with each): tetrahydrofuran, methanol, tetrahydrofuran, dimethylformamide, methanol, dichloromethane, methanol, dimethylformamide.

EXAMPLE 8

Polymer-bound trans-4bromo-N-(4-{2-[4-(2-methoxy-phenyl)-piperazin-1-yl]-ethyl}-cyclohexyl)-benzenesulfonamide To the polymer-bound Trans-4-N-[4-(2-bromo-ethyl)-cyclohexyl]-benzenesulfonamide in 2 ml dimethylformamide 65 mg (5 eq.) 1-(2-methoxyphenyl)-piperazine and 0.065 ml (5 eq.) diisopropylethylamine were added and the mixture was shaken for 18 hours at 90° C. The resin was filtered and washed in sequence with the following solvents (10 ml, twice with each): dimethylformamide, methanol, dimethylformamide, methanol, dimethylformamide, methanol, dichloromethane.

EXAMPLE 9

Trans-4-bromo-N-(4-{2-[4-(2-methoxy-phenyl)-piperazin-1-yl]-ethyl}-cyclohexyl)-benzenesulfonamide The product was cleaved from the resin with shaking in 2 ml of 10% TFA in dichloromethane for two hours. The mixture was filtered and washed with the following solvents (10 ml, twice with each): dichloromethane, methanol, dichloromethane, and methanol. The filtrate was evaporated in vacuo to give the title product.

The LC/MS analysis were performed using an HP 1100 binary gradient system, controlled by ChemStation software. HP diode array detector was used to acquire UV spectra at λ=240 nm. Analytical chromatographic experiments were made on Discovery $C_{16}$-Amide, 5 cm×4.6 mm×5 μm column with a flow rate of 1 ml/min for qualification (purity, capacity factor). All experiments were performed using HP MSD single quadruple mass spectrometer equipped with an electrospray ionisation source to determine the structure.

[k'=$t_R$-$t_0$/$t_0$ $t_R$=retention time
$t_0$=eluent retention time]
k'=capacity factor The following compounds in Table 2 were prepared in a similar manner to Example 5-9:

TABLE 2

| ID | NAME | MW | MS found MW | k' |
|---|---|---|---|---|
| 80001076 | 2,5-Dichloro-N-(4-{2-[4-(3-trifluoromethyl-phenoxy)-piperidin-1-yl]-ethyl}-cyclohexyl)-benzenesulfonamide | 579.5 | 580.4 | 4.272 |
| 80001099 | N-(4-{2-[4-(3-Bromo-phenylamino)-piperidin-1-yl]-ethyl}-cyclohexyl)-4-methoxy-benzenesulfonamide | 550.6 | 551.4 | 3.842 |
| 80001109 | 4-Chloro-N-(4-{2-[4-(3-trifluoromethyl-phenyl)-piperazin-1-yl]-ethyl}-cyclohexyl)-benzenesulfonamide | 530.0 | 530.5 | 3.986 |
| 80001110 | N-(4-{2-[4-(2-Methoxy-phenyl)-piperazin-1-yl]-ethyl}-cyclohexyl)-4-nitro-benzenesulfonamide | 502.6 | 503.5 | 3.545 |
| 80001121 | N-(4-{2-[4-(2,3-Dichloro-phenyl)-piperazin-1-yl]-ethyl}-cyclohexyl)-2-nitro-benzenesulfonamide | 541.5 | 542.5 | 3.942 |
| 80001137 | N-(4-{2-[4-(3-Cyano-5-trifluoromethyl-phenyl)-piperazin-1-yl]-ethyl}-cyclohexyl)-4-fluoro-benzenesulfonamide | 538.6 | 539.5 | 3.859 |
| 80001138 | N-[4-(4-{2-[4-(4-Bromo-2,3-dimethyl-phenyl)-piperazin-1-yl]-ethyl}-cyclohexylsulfamoyl)-phenyl]-acetamide | 591.6 | 592.5 | 3.808 |
| 80001139 | N-(4-{2-[4-(3-Bromo-phenyl)-piperazin-1-yl]-ethyl}-cyclohexyl)-2,4,6-trimethyl-benzenesulfonamide | 548.6 | 549.5 | 4.036 |
| 80001141 | Biphenyl-4-sulfonic acid (4-{2-[4-(4-bromo-2-ethoxy-phenyl)-piperazin-1-yl]-ethyl}-cyclohexyl)-amide | 626.7 | 627.6 | 4.269 |
| 80001153 | N-(4-{2-[4-(2,5-Dichloro-phenylamino)-piperidin-1-yl]-ethyl}-cyclohexyl)-4-nitro-benzenesulfonamide | 555.5 | 556.5 | 4.015 |
| 80001168 | Biphenyl-4-sulfonic acid (4-{2-[4-(5-chloro-2-methoxy-phenyl)-piperazin-1-yl]-ethyl}-cyclohexyl)-amide | 568.2 | 568.6 | 4.104 |
| 80001171 | N-(4-{2-[4-(3-Chloro-phenyl)-piperazin-1-yl]-ethyl}-cyclohexyl)-4-methoxy-benzenesulfonamide | 492.1 | 492.2 | 3.631 |
| 80001181 | N-(4-{2-[4-(3,5-Dichloro-phenyl)-piperazin-1-yl]-ethyl}-cyclohexyl)-4-methyl-benzenesulfonamide | 510.5 | 511.5 | 3.939 |
| 80001187 | N-(4-{2-[4-(4-Chloro-phenyl)-piperazin-1-yl]-ethyl}-cyclohexyl)-4-methoxy-benzenesulfonamide | 492.1 | 493.1 | 3.598 |
| 80001196 | N-(4-{2-[4-(4-Bromo-2-ethoxy-phenyl)-piperazin-1-yl]-ethyl}-cyclohexyl)-4-iodo-benzenesulfonamide | 676.4 | 677.5 | 4.032 |
| 80001210 | 3,4-Dichloro-N-(4-{2-[4-(3-methoxy-biphenyl-4-yl)-piperazin-1-yl]-ethyl}-cyclohexyl)-benzenesulfonamide | 602.6 | 603.5 | 4.230 |
| 80001226 | Quinoline-8-sulfonic acid (4-{2-[4-(3-trifluoromethyl-phenyl)-piperazin-1-yl]-ethyl}-cyclohexyl)-amide | 546.7 | 547.6 | 3.725 |
| 80001233 | N-[4-(4-{2-[4-(3,5-Dichloro-phenyl)-piperazin-1-yl]-ethyl}-cyclohexylsulfamoyl)-phenyl]-acetamide | 553.5 | 554.5 | 3.555 |
| 80001238 | N-(4-{2-[4-(5-Chloro-2-methoxy-phenyl)-piperazin-1-yl]-ethyl}-cyclohexyl)-4-fluoro-benzenesulfonamid | 510.1 | 510.5 | 3.521 |
| 80001239 | N-[4-(4-{2-[4-(3-Chloro-phenyl)-piperazin-1-yl]-ethyl}-cyclohexylsulfamoyl)-phenyl]-acetamide | 519.1 | 519.6 | 3.273 |
| 80001252 | Biphenyl-4-sulfonic acid (4-{2-[4-(2-fluoro-phenyl)-piperazin-1-yl]-ethyl}-cyclohexyl)-amide | 521.7 | 522.6 | 3.985 |
| 80001255 | N-(4-{2-[4-(2-Fluoro-phenyl)-piperazin-1-yl]-ethyl}-cyclohexyl)-4-methoxy-benzenesulfonamide | 475.6 | 476.6 | 3.325 |

TABLE 2-continued

| ID | NAME | MW | MS found MW | k' |
|---|---|---|---|---|
| 80001262 | N-(4-{2-[4-(2-Fluoro-phenyl)-piperazin-1-yl]-ethyl}-cyclohexyl)-4-methyl-benzenesulfonamide | 459.6 | 460.5 | 3.476 |
| 80001264 | N-(4-{2-[4-(5-Chloro-2-methoxy-phenyl)-piperazin-1-yl]-ethyl}-cyclohexyl)-3-trifluoromethyl-benzenesulfonamide | 560.1 | 560.5 | 3.804 |
| 80001271 | N-(4-{2-[4-(4-Chloro-2-methoxy-phenyl)-piperazin-1-yl]-ethyl}-cyclohexyl)-3,4-dimethoxy-benzenesulfonamide | 552.1 | 552.6 | 3.374 |
| 80001276 | N-(4-{2-[4-(2-Fluoro-phenyl)-piperazin-1-yl]-ethyl}-cyclohexyl)-3-nitro-benzenesulfonamide | 490.6 | 491.5 | 3.442 |
| 80001280 | N-(4-{2-[4-(2,3-Dichloro-phenyl)-piperazin-1-yl]-ethyl}-cyclohexyl)-3,4-dimethoxy-benzenesulfonamide | 556.5 | 557.5 | 3.713 |
| 80001294 | N-(4-{2-[4-(4-Chloro-2-methoxy-phenyl)-piperazin-1-yl]-ethyl}-cyclohexyl)-4-methyl-benzenesulfonamide | 506.1 | 506.5 | 3.698 |

EXAMPLE 10

| Pharmaceutical formulation | |
|---|---|
| a) Intravenous injection | |
| Compound of formula (I) | 1-40 mg |
| Buffer | to pH ca 7 |
| Solvent/complexing agent | to 100 ml |
| b) Bolus injection | |
| Compound of formula (I) | 1-40 mg |
| Buffer | to pH ca 7 |
| Co-solvent | to 5 ml |
| Buffer: suitable buffers include e.g. citrate, phosphate, sodium hydroxide/hydrochloric acid. Solvent: typically water but may also include cyclodextrins (1-100 mg) and co-solvents, such as propylene glycol, polyethylene glycol and alcohol. | |
| c) Tablet | |
| Compound of formula (I) | 1-40 mg |
| Diluent/Filter(may also include cyclodextrins) | 50-250 mg |
| Binder | 5-25 mg |
| Disintegrant (may also include cyclodextrins) | 5-50 mg |
| Lubricant | 1-5 mg |
| Cyclodextrin | 1-100 mg |
| Diluent: e.g. mycrocrystalline cellulose, lactose starch. Binder: e.g. polyvinylpyrrolidone, hydroxypropylmethylcellulose. Disintegrant: e.g. sodium starch glycolate, crospovidone. Lubricant: e.g. magnesium stearate, sodium stearyl fumarate | |
| d) Oral suspension | |
| Compound of formula (I) | 1-40 mg |
| Suspending agent | 0.1-10 mg |
| Diluent | 20-60 mg |
| Preservative | 0.01-1.0 mg |
| Buffer | to pH ca 5-8 |
| Co-solvent | 0-40 mg |
| Flavour | 0.01-1.0 mg |
| Colourant | 0.001-0.1 mg |
| Suspending agent: e.g. xanthan gum, mycrocrystalline cellulose. Diluent: e.g. sorbitol solution, typically water. Preservative: e.g. sodium benzoate. Buffer: e.g. citrate. Co-solvent: e.g. alcohol, propylene glycol, polyethylene glycol, cyclodextrin. | |

What we claim:

1. A compound of formula (I)

or a salt thereof, wherein

X represents a nitrogen atom or CH group;

Y represents a bond when X stands for nitrogen, or an oxygen atom or NH or $CH_2$ or $OCH_2$ group when X stands for CH group;

$R_1$, $R_2$, and $R_3$ may be the same or different and represent independently a substituent selected from hydrogen, halogen, $C_{1-6}$-alkyl, $C_{1-6}$ alkoxy, cyano, hydroxy, trifluoromethyl, $C_{1-6}$-alkylsulfonyloxy, trifluoromethanesulfonyloxy, $C_{1-6}$-alkanoyloxy, amino, alkylamino, alkanoylamino, alkylsulfonylamino, arylsulfonylamino, aminocarbonyl, carboxy, N-hydroxycarmamimidoyl, carbamimidoyl, hydroxycarbamoyl, thiocarbamoyl, sulfamoyl, mono or bicyclic heterocyclic group or optionally substituted phenyl, or two adjacent groups of $R_1$, $R_2$, and $R_3$ may combine to form an optionally substituted fused mono or bicyclic heterocyclic group; and Q represents a dialkylamino group or an optionally substituted alkyl, aryl, heteroaryl, aralkyl or heteroaralkyl group wherein "optionally substituted" means, independently at each use, optionally substituted with one or more substituents selected from the group consisting of halogen, cyano, trifluoromethyl, $C_{1-6}$-alkyl, $C_{1-6}$-alkoxy, $C_{1-6}$-alkanoyl, methylenedioxy, $C_{1-6}$-alkylamino, $C_{1-6}$-alkanoylamino, optionally substituted aroyl, aryloxy, aminosulfonyl, arylsulfonylamido, optionally substituted mono or bicyclic aromatic ring, and optionally substituted heteroaromatic ring.

2. A compound according to claim 1 wherein
X represents a nitrogen atom or CH group;
Y represents a bond when X stands for nitrogen, or an oxygen atom or NH or CH$_2$ or OCH$_2$ group when X stands for CH group;
R$_1$, R$_2$, and R$_3$ may be the same or different and represent independently hydrogen, alkyl, alkoxy, halogen, cyano, aminocarbonyl, trifluoromethyl or optionally substituted phenyl or two adjacent groups of R$_1$, R$_2$, and R$_3$ may combine to form an optionally substituted fused mono or bicyclic heterocyclic group; and
Q represents dialkylamino, optionally substituted phenyl, biphenyl, pyridyl, thienyl, alkyl or quinolinyl.

3. A compound according to claim 1 wherein
X represents a nitrogen atom or CH group;
Y represents a bond when X stands for nitrogen, or CH$_2$ group when X stands for CH group;
R$_1$, R$_2$, and R$_3$ may be the same or different and represent independently hydrogen, fluorine, bromine, chlorine atoms or cyano, trifluoromethyl, methyl, methoxy, ethoxy, optionally substituted phenyl or aminocarbonyl groups or two adjacent groups of R$_1$, R$_2$, and R$_3$ may combine to form an optionally substituted fused mono or bicyclic heterocyclic group; and
Q represents C$_{1-4}$ alkyl, dimethylamino, biphenyl, alkylphenyl, alkoxyphenyl, halophenyl, nitrophenyl, trifluoromethylphenyl, aminocarbonylmethylphenyl, pyridyl, or quinolinyl.

4. The compound according to claim 1, wherein said compound is a geometric isomer, a stereoisomer, or a disastereomer.

5. The compound according to claim 1, wherein said compound is a trans-isomer.

6. The compound according to claim 1 selected from the group consisting of
trans-N-(4-{2-[4-(3-cyano-5-trifluoromethylphenyl)piperazin-1-yl]ethyl}-cyclohexyl)pyridine-3-sulfonamide;
trans-N'-(4-{2-[4-(3-methoxybiphenyl-4-yl)piperazin-1-yl]-ethyl}cyclohexyl)-N,N-dimethylsulfamide hydrochloride;
trans-4-chloro-N-(4-{2-[4-(3-cyano-5-trifluoromethylphenyl)piperazin-1-yl]-ethyl}cyclohexyl)benzenesulfonamide hydrochloride;
trans-4-chloro-N-(4-{2-[4-(3-trifluoromethylphenyl)piperazin-1-yl]ethyl}-cyclohexyl)benzenesulfonamide hydrochloride;
trans-N-(4-{2-[4-(3-methoxybiphenyl-4-yl)piperazin-1yl]-ethyl}cyclohexyl)-3-pyridinesulfonamide dihydrochloride;
trans-5-chloro-N-(4-{2-[4-(3-cyano-5-trifluoromethylphenyl)piperazin-1-yl]]-ethyl}cyclohexyl)-2-thiophenesulfonamide hydrochloride;
trans-N'-(4-{2-[4-(3-cyano-5-trifluoromethylphenyl)piperazin-1-yl]ethyl}-cyclohexyl)-N,N-dimethylsulfamide;
trans-N-(4-{2-[4-(3-methoxybiphenyl-4-yl)piperazin-1-yl]ethyl}cyclohexyl)-butanesulfonamide hydrochloride;
trans-N-(4-{2-[4-(3-trifluoromethylphenyl)piperazin-1-yl]ethyl}cyclohexyl)-butanesulfonamide hydrochloride;
trans-N-(4-{2-[4-(3-trifluoromethylphenyl)piperazin-1-yl]ethyl}cyclohexyl)-4-morpholinepropanesulfonamide dihydrochloride;
trans-N-(4-{2-[4-(3-trifluoromethylphenyl)piperazin-1-yl]ethyl}cyclohexyl)-3-pyridinesulfonamide dihydrochloride;
trans-N-(4-{2-[4-(2,3-dichloromethylphenyl)piperazin-1-yl]ethyl}cyclohexyl)-3-pyridinesulfonamide dihydrochloride;
trans-4-bromo-N-(4-{2-[4-(3-trifluoromethylphenylmethyl)piperidin-1-yl]-ethyl}cyclohexyl)benzenesulfonamide;
trans-4-chloro-N-(4-{2-[4-(3-fluorophenylmethyl)piperidin-1-yl]ethyl}-cyclohexyl)benzenesulfonamide;
trans-N-(4-{2-[4-(3-trifluoromethylphenylmethyl)piperidin-1-yl]ethyl}-cyclohexyl)-3-pyridinesulfonamide dihydrochloride;
trans-4-chloro-N-(4-{2-[4-(3-trifluoromethylphenylmethyl)piperidin-1-yl]-ethyl}cyclohexyl)benzenesulfonamide;
trans-4-chloro-N-(4-{2-[4-(3-cyanophenylmethyl)piperidin-1-yl]ethyl}-cyclohexyl)benzenesulfonamide hydrochloride;
trans-N-(4-{2-[4-(3-trifluoromethylphenylamino)piperidin-1-yl ]ethyl}-cyclohexyl)trifluoroethanesulfonamide hydrochloride;
trans-N-(4-{2-[4-(3-trifluoromethylphenylamino)piperidin-1-yl]ethyl}-cyclohexyl)butanesulfonamide hydrochloride;
trans-4-chloro-N-(4-{2-[4-(3-trifluoromethylphenylamino)piperidin-1-yl]ethyl}-cyclohexyl)benzenesulfonamide hydrochloride;
trans-N'-(4-{2-[4-(3-trifluoromethylphenylamino)piperidin-1-yl]ethyl}-cyclohexyl)-N,N-dimethylsulfamide hydrochloride;
trans-N-(4-{2-[4-(3-trifluoromethylphenylmethoxy)piperidin-1-yl]ethyl}-cyclohexyl)-3-pyridinesulfonamide dihydrochloride;
trans-N-(4-{2-[4-(3-trifluoromethylphenoxy)piperidin-1-yl]ethyl}cyclohexyl)-3-pyridinesulfonamide dihydrochloride; and
trans-N-{4-[2-[4-(3-aminocarbonyl-5-trifluoromethylphenyl)-1-piperizinyl]-ethyl]cyclohexyl}-3-pyridinesulfonamide.

7. A compound according to claim 1 selected from the group consisting of
trans-4-bromo-N-(4-{2-[4-(2-methoxyphenyl)piperazin-1-yl]ethyl}cyclohexyl)-benzenesulfonamide;
2,5-dichloro-N-(4-{2-[4-(3-trifluoromethylphenoxy)piperidin-1-yl]ethyl}-cyclohexyl)benzenesulfonamide;
N-(4-{2-[4-(3-bromophenylamino)piperidin-1-yl]ethyl}cyclohexyl)-4-methoxy-benzenesulfonamide;
4-chloro-N-(4-{2-[4-(3-trifluoromethylphenyl)piperazin-1-yl]ethyl}-cyclohexyl)benzenesulfonamide;
N-(4-{2-[4-(2-methoxyphenyl)piperazin-1-yl]ethyl}cyclohexyl)-4-nitro-benzenesulfonamide;
N-(4-{2-[4-(2,3-dichlorophenyl)piperazin-1-yl]ethyl}cyclohexyl)-2-nitro-benzenesulfonamide;
N-(4-{2-[4-(3-cyano-5-trifluoromethylphenyl)piperazin-1-yl]ethyl}cyclohexyl)-4-fluorobenzenesulfonamide;
N-[4-(4-{2-[4-(4-bromo-2,3-dimethylphenyl)piperazin-1-yl]ethyl}cyclohexyl-sulfamoyl)phenyl]acetamide;
N-(4-{2-[4-(3-bromophenyl)piperazin-1-yl]ethyl}cyclohexyl)-2,4,6-trimethyl-benzenesulfonamide;
biphenyl-4-sulfonic acid (4-{2-[4-(4-bromo-2-ethoxyphenyl)piperazin-1-yl]-ethyl}cyclohexyl)amide;
N-(4-{2-[4-(2,5-dichlorophenylamino)piperidin-1-yl]ethyl}cyclohexyl)-4-nitro-benzenesulfonamide;
biphenyl-4-sulfonic acid (4-{2-[4-(5-chloro-2-methoxyphenyl)piperazin-1-yl]ethyl}cyclohexyl)amide;
N-(4-{2-[4-(3-chlorophenyl)piperazin-1-yl]ethyl}cyclohexyl)-4-methoxy-benzenesulfonamide;

N-(4-{2-[4-(3,5-dichlorophenyl)piperazin-1-yl]
ethyl}cyclohexyl)-4-methyl-benzenesulfonamide;
N-(4-{2-[4-(4-chlorophenyl)piperazin-1-yl]
ethyl}cyclohexyl)-4-methoxy-benzenesulfonamide;
N-(4-{2-[4-(4-bromo-2-ethoxyphenyl)piperazin-1-yl]
ethyl}cyclohexyl)-4-iodo-benzenesulfonamide;
3,4-dichloro-N-(4-{2-[4-(3-methoxybiphenyl-4-yl)piperazin-1-yl]ethyl}-cyclohexyl)benzenesulfonamide;
quinoline-8-sulfonic acid (4-{2-[4-(3-trifluoromethylphenyl)piperazin-1-yl]-ethyl}cyclohexyl)amide;
N-[4-(4-{2-[4-(3,5-dichlorophenyl)piperazin-1-yl]
ethyl}cyclohexylsulfamoyl)-phenyl]acetamide;
N-(4-{2-[4-(5-chloro-2-methoxyphenyl)piperazin-1-yl]
ethyl}cyclohexyl)4-fluorobenzenesulfonamide;
N-[4-(4-{2-[4-(3-chlorophenyl)piperazin-1-yl]-
ethyl}cyclohexylsulfamoyl)-phenyl]acetamide;
biphenyl-4-sulfonic acid (4-{2-[4-(2-fluorophenyl)piperazin-1-yl]ethyl}-cyclohexyl)amide;
N-(4-{2-[4-(2-fluorophenyl)piperazin-1-yl]
ethyl}cyclohexyl)-4-methoxy-benzenesulfonamide;
N-(4-{2-[4-(2-fluorophenyl)piperazin-1-yl]
ethyl}cyclohexyl)-4-methyl-benzenesulfonamide;
N-(4-{2-[4-(5-chloro-2-methoxyphenyl)piperazin-1-yl]
ethyl}cyclohexyl)-3-trifluoromethylbenzene-
sulfonamide;
N-(4-{2-[4-(4-chloro-2-methoxyphenyl)piperazin-1-yl]
ethyl)}cyclohexyl)-3,4-dimethoxy-benzenesulfona-
mide;
N-(4-{2-[4-(2-fluorophenyl)piperazin-1-yl]
ethyl}cyclohexyl)-3-nitro-benzenesulfonamide;
N-(4-{2-[4-(2,3-dichlorophenyl)piperazin-1-yl]
ethyl}cyclohexyl)-3,4-dimethoxy-benzenesulfona-
mide; and
N-(4-{2-[4-(4-chloro-2-methoxyphenyl)piperazin-1-yl]
ethyl}cyclohexyl)-4-methylbenzenesulfonamide.

8. A process for preparing a compound according to any one of claims 1-3 and 4-7 which comprises reacting a compound of formula (II)

wherein Q is as hereinbefore defined
with a compound of formula (III)

wherein $R_1$, $R_2$, $R_3$, X and Y are as hereinbefore defined; and
optionally, separating enantiomers, diastereomers, cis- and trans-isomers, and mixtures thereof of a compound according to any one of claims 1-3 and 4-7;
thereby obtaining the compound according to any one of claims 1-3 and 4-7.

9. A pharmaceutical composition comprising a compound according to any one of claims 1-3 and 4-7 and one or more physiologically acceptable carriers.

10. A method of treating a neuropsychiatric condition said method comprising administering to a mammalian subject in need thereof an effective amount of a compound according to any of claims 1-3 and 4-7.

11. A process for preparing a compound according to claim 1 comprising
i) reacting a compound of formula (VI)

wherein $R_6$ represents hydrogen or a protecting group,
with a polystyrene resin of formula (V)

wherein $R_4$ and $R_5$ can be the same or different and represent hydrogen or methoxy group provided that both $R_4$ and $R_5$ are not hydrogen, by reductive amination with a reducing agent;
ii) halogenation of the terminal hydroxy group of a compound of formula (VII)

wherein the meaning of $R_6$ is as described above for formula (VI), with a halogenation agent, or if it was protected, the protecting group having been removed before the halogenation, which results in a solid phase compound of formula (VIII)

wherein Z represents a halogen and the meaning of $R_4$ and $R_5$ is as described above for formula (V);
iii) sulfonylation a compound of formula (VIII) with a sulfonylchloride of formula(II)

wherein the meaning of Q is as described above for formula (I) to form a compound of formula (IX)

iv) alkylation of the compound of formula (IX) with a compound of formula (IV)

wherein the meaning of Z, $R_4$ and $R_5$ are as described above for the formula (VIII) and the meaning of Q is as described above for formula (I) of a secondary amine of formula (IV) wherein the meaning of $R_1$, $R_2$, $R_3$, X and Y are as described above for the formula (I); and v) releasing the products of formula (I) from the solid-phase compound of formula (X)

wherein the meaning of Q, $R_1$, $R_2$, $R_3$, $R_4$, $R_5$, X and Y are as described above for the formula (I) by acidic cleavage.

12. The method according to claim 10 wherein the compound is an agonist of a dopamine $D_3$ receptor.

13. The method according to claim 8 wherein the compound of formula (III) is selected from the group consisting of
trans-3-{4-[2-(4-aminocyclohexyl)ethyl]piperazin-1-yl}-5-trifluoromethyl-benzonitrile;
trans-4-{2-[4-(3-methoxybiphenyl-4-yl)-piperazin-1-yl]ethyl}cyclohexylamine dihydrochloride;
trans-4-{2-[4-(3-trifluoromethylphenyl)piperazin-1-yl]ethyl}cyclohexylamine dihydrochloride;
trans-4-{2-[4-(2,3-dichloro-phenyl)piperazin-1-yl]ethyl}cyclohexylamine dihydrochloride;
trans-4-{2-[4-(3-trifluoromethylphenylmethyl)piperidin-1-yl]-ethyl}-cyclohexylamine dihydrochloride;
trans-4-{2-[4-(3-fluoro-phenylmethyl)piperidin-1-yl]ethyl}cyclohexylamine dihydrochloride;
trans-4-{2-[4-(3-cyanophenylmethyl)piperidin-1-yl]ethyl}cyclohexylamine dihydrochloride;
trans-4-{2-[4-(3-trifluoromethylphenylamino)piperidin-1-yl]ethyl}-cyclohexylamine dihydrochloride;
trans-4-{2-[4-(3-trifluoromethylphenylmethoxy)piperidin-1-yl]ethyl}-cyclohexylamine dihydrochloride; and
trans-4-{2-[4-(3-trifluoromethylphenoxy)piperidin-1-yl]ethyl}cyclohexylamine dihydrochloride.

14. The process according to claim 8, further comprising converting the compound obtained from the process of claim 8 to a second compound of formula I, wherein the conversion comprises converting one of $R_1$, $R_2$, and $R_3$:
a) from an alkoxy group to a hydroxy group;
b) from a hydroxy group to an alkoxy group;
c) from a cyano group to an amide group;
d) from a cyano group to an amidine group; or
e) from a hydrogen to a halogen.

15. The pharmaceutical composition according to claim 9, wherein the composition comprises a compound according to claim 1 and water.

16. The method according to claim 10 wherein said compound is an antagonist of a dopamine $D_3$ receptor.

17. The method according to claim 10 wherein the compound is a partial agonist of a dopamine $D_3$ receptor.

18. The method according to claim 10 wherein the condition is Parkinson's disease.

19. The compound according to claim 1, wherein Q is pyridyl and $R_1$, $R_2$, and $R_3$ are independently selected from the group consisting of hydrogen, cyano, and trifluoromethyl.

20. The compound according to claim 1, which is trans-N-(4-{2-[4-(3-cyano-5-trifluoromethylphenyl)piperazin-1-yl]ethyl}-cyclohexyl)pyridine-3-sulfonamide.

21. The method according to claim 10, wherein the neuropsychiatric condition is selected from the group consisting of schizophrenia, schizo-affective disorder, psychotic depression, mania, paranoid, and delusional disorders, Parkinson's disease, and neuroleptic induced parkinsonism.

22. The method according to claim 10, wherein the neuropsychiatric condition is schizophrenia.

\* \* \* \* \*